US012591987B2

(12) United States Patent
Low et al.

(10) Patent No.: US 12,591,987 B2
(45) Date of Patent: Mar. 31, 2026

(54) SYSTEM AND METHOD FOR SIMULTANEOUSLY REGISTERING MULTIPLE LUNG CT SCANS FOR QUANTITATIVE LUNG ANALYSIS

(71) Applicant: The Regents of the University of California, Oakland, CA (US)

(72) Inventors: Daniel A. Low, Los Angeles, CA (US); Dan Ruan, Los Angeles, CA (US); Anand Santhanam, Northridge, CA (US)

(73) Assignee: The Regents of the University of California, Oakland, CA (US)

( * ) Notice: Subject to any disclaimer, the term of this patent is extended or adjusted under 35 U.S.C. 154(b) by 304 days.

(21) Appl. No.: 18/565,826

(22) PCT Filed: Jun. 1, 2022

(86) PCT No.: PCT/US2022/031801
§ 371 (c)(1),
(2) Date: Nov. 30, 2023

(87) PCT Pub. No.: WO2022/256421
PCT Pub. Date: Dec. 8, 2022

(65) Prior Publication Data
US 2024/0371013 A1 Nov. 7, 2024

Related U.S. Application Data

(60) Provisional application No. 63/195,371, filed on Jun. 1, 2021.

(51) Int. Cl.
*G06T 7/38* (2017.01)
*A61B 6/03* (2006.01)
(Continued)

(52) U.S. Cl.
CPC ................ *G06T 7/38* (2017.01); *A61B 6/032* (2013.01); *A61B 6/50* (2013.01); *G06T 7/0012* (2013.01);
(Continued)

(58) Field of Classification Search
CPC .................... G06T 7/38; G06T 7/0012; G06T 2207/10081; G06T 2207/30061;
(Continued)

(56) References Cited

U.S. PATENT DOCUMENTS 9,076,201 B1 * 7/2015 Negahdar ................. G06T 7/38
9,760,989 B2 * 9/2017 Yin ........................ G16H 50/30
(Continued)

OTHER PUBLICATIONS

Hering, A. et al., Unsupervised Learning for Large Motion Thoracic CT Follow-Up Registration, in Medical Imaging 2019: Image Processing, Proc. of SPIE, 2019, vol. 10949, pp. 331-337.
(Continued)

*Primary Examiner* — Bobbak Safaipour
(74) *Attorney, Agent, or Firm* — Quarles & Brady LLP

(57) ABSTRACT

A method for simultaneously registering a plurality of computed tomography (CT) scans of a region of interest of a subject including a subject's lungs for quantitative lung analysis includes receiving a plurality of CT scans of the region of interest acquired with a CT imaging system, receiving a breathing surrogate data for the subject, the breathing surrogate data comprising an amplitude for each of the plurality of CT scans and determining a deformation based on the plurality of CT scans and the breathing surrogate data using an iterative optimization process of an objective function. The objective function can include a first term based on an approximation of local changes in Hounsfield Units (HU) adjusted for breathing of the subject and a second term based on error in the conservation of (Continued)

mass. At least one quantitative lung parameter may be determined based on the deformation.

23 Claims, 8 Drawing Sheets

(51) Int. Cl.
*A61B 6/50* (2024.01)
*G06T 7/00* (2017.01)

(52) U.S. Cl.
CPC ............... *G06T 2207/10081* (2013.01); *G06T 2207/30061* (2013.01)

(58) Field of Classification Search
CPC .. G06T 7/30; A61B 6/032; A61B 6/50; A61B 6/5235; A61B 6/5288; A61B 5/113
See application file for complete search history.

(56) References Cited

U.S. PATENT DOCUMENTS

| | | | |
|---|---|---|---|
| 10,628,963 B2 * | 4/2020 | Bertram | G06T 7/90 |
| 2016/0113614 A1 | 4/2016 | Cetingul et al. | |
| 2018/0068446 A1 * | 3/2018 | Ross | G06T 7/136 |
| 2019/0012805 A1 | 1/2019 | Bertram et al. | |
| 2021/0074007 A1 | 3/2021 | Low et al. | |
| 2025/0268601 A1 * | 8/2025 | Mathis | A61B 1/01 |

OTHER PUBLICATIONS

Lafreniere, M. et al., Continuous Generation of Volumetric Images During Stereotactic Body Radiation Therapy Using Periodic kV Imaging and an External Respiratory Surrogate, arXiv:1808.08310, 2019, pp. 1-12.
European Patent Office, Extended Search Report, Application No. 22816785.4, Mar. 17, 2025, 6 pages.
Castillo, E. et al., Four-Dimensional Deformable Image Registration Using Trajectory Modeling, Physics in Medicine & Biology, 2010, 55(1):305-327.
Castillo, E. et al., Robust CT Ventilation from the Integral Formulation of the Jacobian, Medical Physics, 2019, 46(5):2115-2125.
Castillo, R. et al., A Framework for Evaluation of Deformable Image Registration Spatial Accuracy Using Large Landmark Point Sets, Physics in Medicine & Biology, 2009, 54(7):1849-1870.
Ding, K. et al., Comparison of Image Registration Based Measures of Regional Lung Ventilation from Dynamic Spiral CT with Xe-CT, Medical Physics, 2012, 39(8):5084-5098.
Dou, T. et al., A Method for Assessing Ground-Truth Accuracy of the 5DCT Technique, International Journal of Radiation Oncology Biology Physics, 2015, 93(4):925-933.
Duarte, S. et al., Use of 4D-CT for Radiotherapy Planning and Reality in France: Data from a National Survey, Cancer/ Radiotherapie, 2019, 23(5):395-400.
Foote, M. et al., Rank Constrained Diffeomorphic Density Motion Estimation for Respiratory Correlated Computed Tomography, arXiv:1909.11841, 2019, pp. 1-10.
Gorbunova, V. et al., Mass Preserving Image Registration for Lung CT, Medical Image Analysis, 2012, 16(4):786-795.
Guerrero, T. et al., Quantification of Regional Ventilation from Treatment Planning CT, International Journal of Radiation Oncology Biology Physics, 2005, 62(3):630-634.
Guerrero, T. et al., Dynamic Ventilation Imaging from Four-Dimensional Computed Tomography, Physics in Medicine & Biology, 2006, 51(4):777-791.
Kipritidis, J. et al., The Vampire Challenge: A Multi-Institutional Validation Study of CT Ventilation Imaging, Medical Physics, 2019, 46(3):1198-1217.
Low, D. et al., A Method for the Reconstruction of Four-Dimensional Synchronized CT Scans Acquired During Free Breathing, Medical Physics, 2003, 30(6):1254-1263.
Low, D. et al., Novel Breathing Motion Model for Radiotherapy, International Journal of Radiation Oncology Biology Physics, 2005, 63(3):921-929.
Low, D. et al., A Novel CT Acquisition and Analysis Technique for Breathing Motion Modeling, Phys Med Biol, 2013, 58(11):L-31-L-36.
Lu, W. et al., Comparison of Spirometry and Abdominal Height as Four-Dimensional Computed Tomography Metrics in Lung, Medical Physics, 2005, 32(7):2351-2357.
O'Connell, D. et al., A Prospective Gating Method to Acquire a Diverse Set of Free-Breathing CT Images for Model-Based 4DCT, Physics in Medicine & Biology, 2018, 63:04NT03, 10 pages.
O'Connell, D. et al., Safety-Oriented Design of In-House Software for New Techniques: A Case Study Using a Model-Based 4DCT Protocol, Medical Physics, 2019, 46(4):1523-1532.
Reinhardt, J. et al., Registration-Based Estimates of Local Lung Tissue Expansion Compared to Xenon CT Measures of Specific Ventilation, Medical Image Analysis, 2008, 12(6):752-763.
Shao, W. et al., N-Phase Local Expansion Ratio for Characterizing Out-of-Phase Lung Ventilation, IEEE Transactions on Medical Imaging, 2020, 39(6):2025-2034.
Simon, B., Non-Invasive Imaging of Regional Lung Function Using X-ray Computed Tomography, Journal of Clinical Monitoring and Computing, 2000, 16:433-442.
Thomas, D. et al., A Novel Fast Helical 4D-CT Acquisition Technique to Generate Low-Noise Sorting Artifact-Free Images at User-Selected Breathing Phases, International Journal of Radiation Oncology Biology Physics, 2014, 89(1):191-198.
Thomas, D. et al., Investigating the Minimum Scan Parameters Required to Generate Free-Breathing Motion Artefact-Free Fast-Helical CT, British Journal of Radiology, 2018, 91(1082):20170597, pp. 1-8.
Ugander, M. et al., Pulmonary Intravascular Blood Volume Changes Through the Cardiac Cycle in Healthy Volunteers Studied by Cardiovascular Magnetic Resonance Measurements of Arterial and Venous Flow, Journal of Cardiovascular Magnetic Resonance, 2009, 11:42, pp. 1-8.
Mnogradskiy, Y., CT-Based Ventilation Imaging in Radiation Oncology, BJR Open, 2019, 1:20180035, pp. 1-8.
Vishnevskiy, V. et al., Isotropic Total Variation Regularization of Displacements in Parametric Image Registration, IEEE Transactions on Medical Imaging, 2016, 36(2):385-395.
Watkins, W. et al., Patient-Specific Motion Artifacts in 4DCT, Medical Physics, 2010, 37(6):2855-2861.
Yamamoto, T. et al., Reproducibility of Four-dimensional Computed Tomography-based Lung Ventilation Imaging, Academic Radiology, 2012, 19(12):1554-1565.
Yang, D. et al., 4D-CT Motion Estimation Using Deformable Image Registration and 5D Respiratory Motion Modeling, Med Phys, 2008, 35(10):4577-4590.
PCT International Search Report and Written Opinion, PCT/US2022/ 031801, Oct. 12, 2022, 11 pages.

* cited by examiner

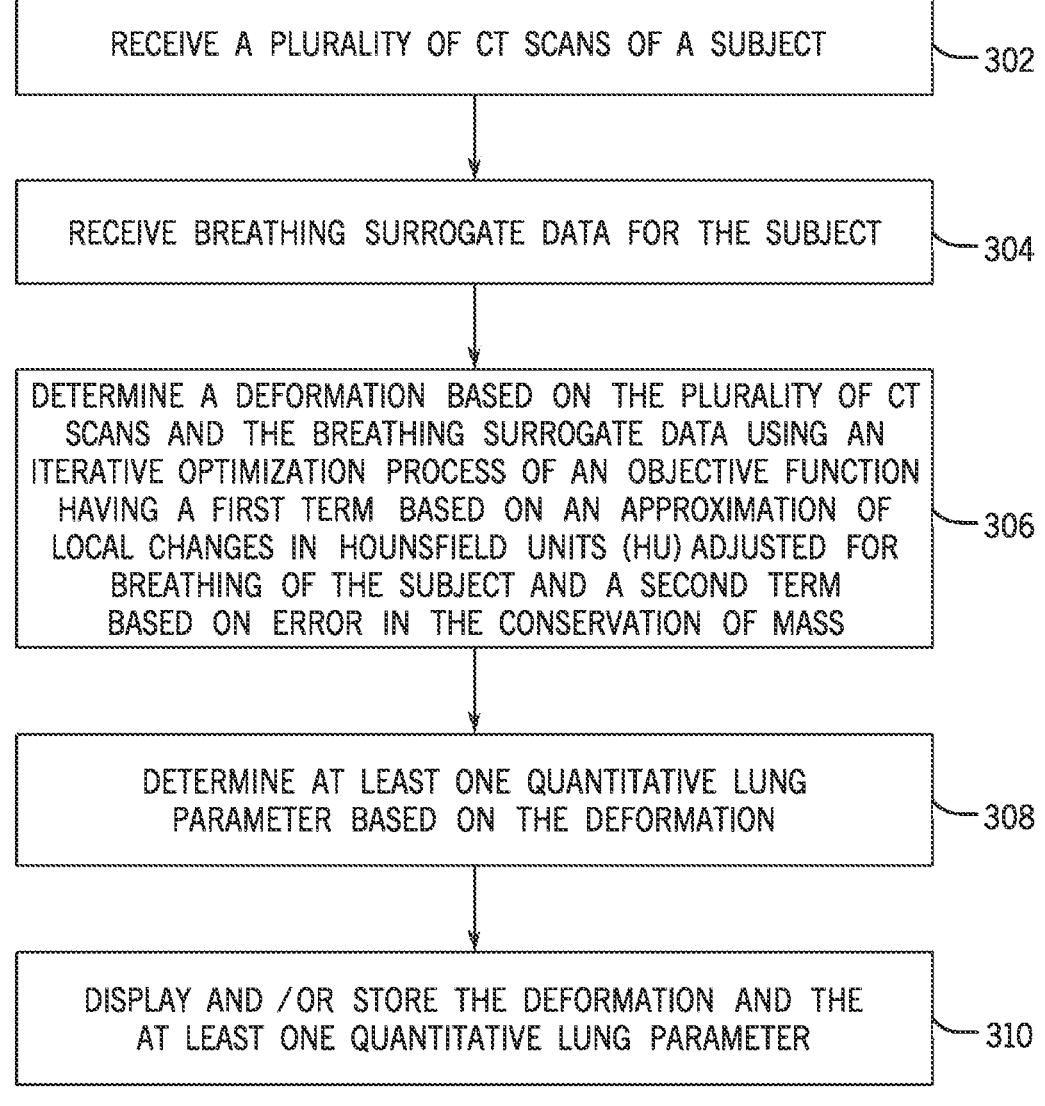

RECEIVE A PLURALITY OF CT SCANS OF A SUBJECT ⎯302

RECEIVE BREATHING SURROGATE DATA FOR THE SUBJECT ⎯304

DETERMINE A DEFORMATION BASED ON THE PLURALITY OF CT SCANS AND THE BREATHING SURROGATE DATA USING AN ITERATIVE OPTIMIZATION PROCESS OF AN OBJECTIVE FUNCTION HAVING A FIRST TERM BASED ON AN APPROXIMATION OF LOCAL CHANGES IN HOUNSFIELD UNITS (HU) ADJUSTED FOR BREATHING OF THE SUBJECT AND A SECOND TERM BASED ON ERROR IN THE CONSERVATION OF MASS ⎯306

DETERMINE AT LEAST ONE QUANTITATIVE LUNG PARAMETER BASED ON THE DEFORMATION ⎯308

DISPLAY AND /OR STORE THE DEFORMATION AND THE AT LEAST ONE QUANTITATIVE LUNG PARAMETER ⎯310

FIG. 3A

SELECT A REFERENCE SCAN FROM THE PLURALITY OF CT SCANS — 312

RECEIVE AN INITIAL DEFORMATION VECTOR FIELD — 314

DETERMINE, FOR THE PLURALITY OF CT IMAGES, A DEFORMATION VECTOR FIELD THAT MINIMIZES THE OBJECTIVE FUNCTION USING THE ITERATIVE OPTIMIZATION PROCESS — 316

STORE THE DETERMINED DEFORMATION VECTOR FIELD — 318

SYSTEM AND METHOD FOR SIMULTANEOUSLY REGISTERING MULTIPLE LUNG CT SCANS FOR QUANTITATIVE LUNG ANALYSIS

CROSS-REFERENCES TO RELATED APPLICATIONS

This application represents the national stage entry of PCT/US2022/031801 filed on Jun. 1, 2022 and claims the benefit of U.S. Provisional Patent Application Ser. No. 63/195,371 filed on Jun. 1, 2021, the contents of which is incorporated herein by reference as if set forth in its entirety for all purposes.

BACKGROUND

Human lungs have two primary purposes, transporting air and gas exchange. The dynamic and quasi-voluntary nature of breathing make imaging of lungs challenging. Computed tomography (CT) is a useful 3D high resolution free-breathing lung imaging modality. Registration of lung CT scans may be used for numerous purposes. Because lung function is fundamentally connected with its motion and distortion, CT image registration is critical to the quantitative understanding and characterization of lung function. CT data and image registration can be used to measure and describe lung motion, breathing dynamics, biomechanical properties, and other structural and functional properties.

CT-based lung function imaging has traditionally been conducted using breath-hold. While breath-hold CT provides images without motion-induced or sorting artifacts, it suffers from the inability to be sensitive to dynamic processes and often involves images at deep inhalation and exhalation, causing large deformations that are difficult to register. An alternative approach has been the use of four-dimensional CT (4DCT), which has been utilized with a series of challenges to extract ventilation information. While 4DCT is used extensively for treatment planning when tumors are affected by breathing motion, 4DCT suffers from breathing sorting artifacts and an inability to determine the accuracy of the relationship between the resulting images and the motion of the lung tissue which interfere with its use in quantitative lung dynamics analysis. The breathing sorting artifacts present in 4DCT complicate and hinder functional measurements. Typically, deformable image registration is used to define a deformation vector field (DVF) that in turn can be used to calculate local tissue expansion and variations in Hounsfield Units (HUs) and thereby tissue density. The local expansion, which has been considered a measurement of ventilation, is described using the DVF Jacobian. Even small 4DCT sorting errors will cause relatively large errors in the calculation of the Jacobian and consequently the ventilation.

The fundamental reason that 4DCT has such sorting artifacts is the limited temporal sampling afforded by conventional 4DCT approaches. 4DCT is acquired using either low-pitch helical acquisition or repeated cine acquisition, wherein in either case, the CT data for any region of the body are acquired over approximately 8 seconds, enough time to encompass between one and two breaths. The theory behind this is that as long as there are CT data for each breath, the CT scans can be reconstructed at any selected breathing phase. The limitation of this assumption is that of breathing regularity, which for many patients is insufficient to provide DVFs sufficiently artifact-free to provide artifact-free CT images or support ventilation measurements.

Because of the limitations of 4DCT, prior approaches may select repeated fast-helical free-breathing CT (FHFBCT) to provide the image data for radiation therapy treatment planning, referred to as 5DCT. FHFBCT is a shorthand for conventional helical CT that employs parameters such as gantry rotation speed and pitch that provide the maximum couch speed available from that CT scanner. Repeated FHFBCT allows acquisition of image data at each couch position spread out over many seconds to minutes (depending on the amount of time between successive scans), distributing the acquired image data over multiple breaths, and improving the chances that the image data are acquired at a representative range of breathing depths and rates. 5DCT involves the generation of a breathing motion model that ties together the patient geometries measured by the set of FHFBCT scans, and although the 5D motion model has been shown in general to be accurate to within approximately 3 mm, that accuracy is assumed to be insufficient for ventilation measurements.

It would be desirable to provide a system and method for registering a plurality of CT images and performing quantitative lung analysis that overcome the challenges of prior CT image registration approaches such as, for example, sorting artifacts.

SUMMARY

In accordance with an embodiment, a method for simultaneously registering a plurality of computed tomography (CT) scans of a region of interest of a subject including a subject's lungs for quantitative lung analysis includes receiving a plurality of CT scans of the region of interest acquired with a CT imaging system, receiving a breathing surrogate data for the subject, the breathing surrogate data comprising an amplitude for each of the plurality of CT images and determining a deformation based on the plurality of CT scans and the breathing surrogate data using an iterative optimization process of an objective function. The objective function can include a first term based on an approximation of local changes in Hounsfield Units (HU) adjusted for breathing of the subject and a second term based on error in the conservation of mass.

In accordance with an embodiment, a system for simultaneously registering a plurality of computed tomography (CT) scans of a region of interest of a subject including a subject's lungs for quantitative lung analysis includes a processor device and a non-transitory computer-readable memory storing instructions executable by the processor device. The instructions, when executed by the processor device, can cause the system to receive a plurality of CT scans of the region of interest acquired with a CT imaging system, receive a breathing surrogate data for the subject, the breathing surrogate data comprising an amplitude for each of the plurality of CT scans and determine a deformation based on the plurality of CT images and the breathing surrogate data using an iterative optimization process of an objective function. The objective function can include a first term based on an approximation of local changes in Hounsfield Units (HU) adjusted for breathing of the subject and a second term based on error in the conservation of mass.

BRIEF DESCRIPTION OF THE DRAWINGS

FIGS. 3A and 3B illustrate a method for simultaneously registering a plurality of CT scans of a region of interest of a subject for quantitative lung analysis in accordance with an embodiment;

DETAILED DESCRIPTION

Figure 1A:
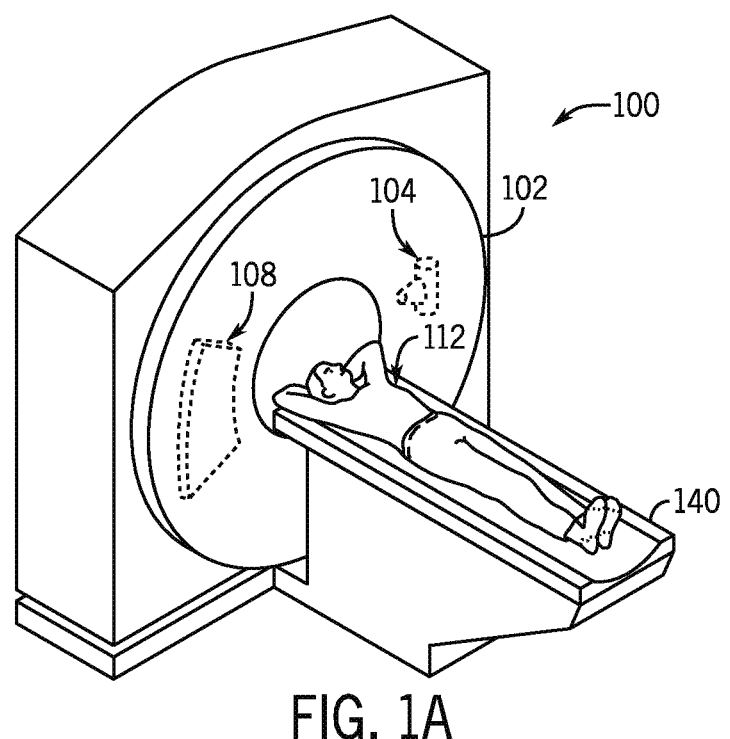
FIG. 1A is an illustration of an example of an x-ray computed tomography (CT) system in accordance with an embodiment.
Figure 1B:
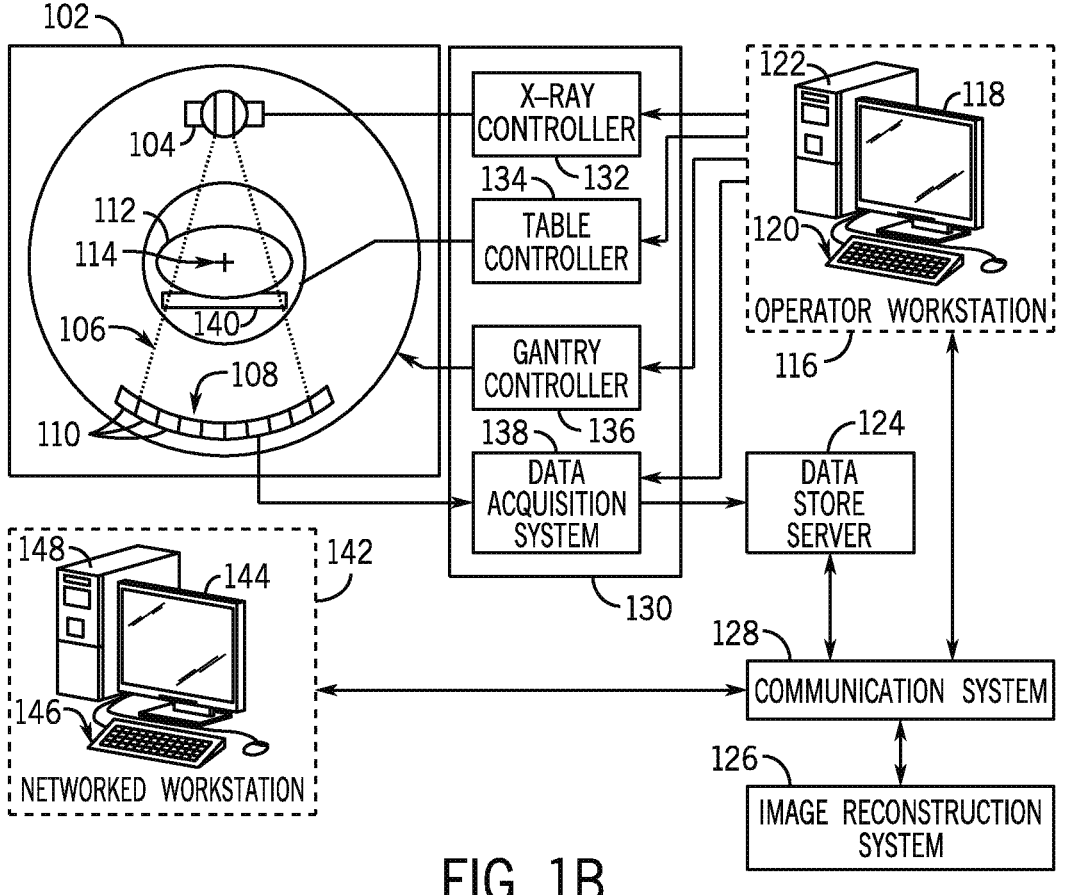
FIG. 1B is a block diagram of the example x-ray CT system of FIG. 6A in accordance with an embodiment.

FIGS. 1A and 1B show an example of a computer tomography (CT) system 100 that may be used to perform the methods described herein. The CT system 100 includes a gantry 102, to which at least one x-ray source 104 is coupled. The x-ray source 104 projects an x-ray beam 106, which may be a fan-beam or cone-beam of x-rays, towards a detector array 108 on the opposite side of the gantry 102. The detector array 108 includes a number of x-ray detector elements 110. Together, the x-ray detector elements 110 sense the projected x-rays 106 that pass through a subject 112, such as a medical patient or an object undergoing examination, that is positioned in the CT system 100. Each x-ray detector element 110 produces an electrical signal that may represent the intensity of an impinging x-ray beam and, hence, the attenuation of the beam as it passes through the subject 112. In some configurations, each x-ray detector 110 is capable of counting the number of x-ray photons that impinge upon the detector 110. During a scan to acquire x-ray projection data, the gantry 102 and the components mounted thereon rotate about a center of rotation 114 within the CT system 100.

The CT system 100 also includes an operator workstation 116, which typically includes a display 118; one or more input devices 120, such as a keyboard and mouse; and a computer processor 122. The computer processor 122 may include a commercially available programmable machine running a commercially available operating system. The operator workstation 116 provides the operator interface that enables scanning control parameters to be entered into the CT system 100. In general, the operator workstation 116 is in communication with a data store server 124 and an image reconstruction system 126. By way of example, the operator workstation 116, data store server 124, and image reconstruction system 126 may be connected via a communication system 128, which may include any suitable network connection, whether wired, wireless, or a combination of both. As an example, the communication system 128 may include both proprietary or dedicated networks, as well as open networks, such as the internet.

The operator workstation 116 is also in communication with a control system 130 that controls operation of the CT system 100. The control system 130 generally includes an x-ray controller 132, a table controller 134, a gantry controller 136, and a data acquisition system (DAS) 138. The x-ray controller 132 provides power and timing signals to the x-ray source 104 and the gantry controller 136 controls the rotational speed and position of the gantry 102. The table controller 134 controls a table 140 to position the subject 112 in the gantry 102 of the CT system 100.

The DAS 138 samples data from the detector elements 110 and converts the data to digital signals for subsequent processing. For instance, digitized x-ray data is communicated from the DAS 138 to the data store server 124. The image reconstruction system 126 then retrieves the x-ray data for a scan from the data store server 124 and reconstructs one or more slices (or images) therefrom. The image reconstruction system 126 may include a commercially available computer processor, or may be a highly parallel computer architecture, such as a system that includes multiple-core processors and massively parallel, high-density computing devices. Optionally, image reconstruction can also be performed on the processor 122 in the operator workstation 116. Reconstructed slices (or images) for a scan can then be communicated back to the data store server 124 for storage or to the operator workstation 116 to be displayed to the operator or clinician.

The CT system 100 may also include one or more networked workstations 142. By way of example, a networked workstation 142 may include a display 144; one or more input devices 146, such as a keyboard or mouse; and a processor 148. The networked workstation 142 may be located within the same facility as the operator workstation 116, or a different facility, such as a different healthcare institution or clinic.

The networked workstation 142, whether within the same facility or in a different facility as the operator workstation 116, may gain remote access to the data store server 124 and/or the image reconstruction system 126 via the communication system 128. Accordingly, multiple networked workstations 142 may have access to the data store server 124 and/or image reconstruction system 126. In this manner, x-ray data, reconstructed slices (or images), or other data may be exchanged between the data store server 124, the image reconstruction system 126, and the networked workstations 142, such that the data or slices may be remotely processed by a networked workstation 142. This data may be exchanged in any suitable format, such as in accordance with the transmission control protocol ("TCP"), the internet protocol ("IP"), or other known or suitable protocols.

The present disclosure describes a system and method for simultaneously registering a plurality of CT scans of a region of interest for quantitative lung analysis of a subject. The system and method can be used to generate quantitative image-based analysis of the lungs and breathing of a subject. Advantageously, fundamental physical principles may be used to drive the registration. In some embodiments, a plurality of CT scans are registered using an objective function with two terms, namely, a first term based on an approximation of local changes in Hounsfield Units (HU) adjusted for breathing of the subject (i.e., a ventilation adjusted (or corrected) HU difference) and a second term based on error in the conservation of mass. In some embodiments, the second term is based on the difference between the deformation Jacobian and the tissue density ratio. A deformation for the plurality of CT scans may be determined using an iterative optimization process of the objective function, for example, to determine a deformation such that the objective function is minimized. In some embodiments, the deformation is a deformation vector field (DVF). The determined deformation may be used to determine or estimate one or more quantitative lung parameters such as, for example, ventilation measurements (e.g., local tissue expansion), lung motion measurements and description, breathing dynamics, biomechanical properties, and other structural and functional properties. In some embodiments, ventilation may be calculated voxel-by-voxel as the slope of a first order fit of the deformation Jacobian (or Jacobian DVF) as a function of the breathing amplitude. Accordingly, the plurality of CT scans may be used directly to measure ventilation. In some embodiments, the techniques described herein may be used to measure high spatial resolution dynamic ventilation processes.

In some embodiments, the plurality of CT scans are free-breathing CT scans acquired using a free-breathing CT acquisition protocol such as, for example, fast helical free-breathing CT (FHFBCT) scans. Advantageously, FHFBCT scans do not have sorting artifacts and can include relatively small motion induced by quiet respiration. In addition, free-breathing scans may enable characterizing dynamic breathing processes that disappear during breath hold. In addition, because the CT data may be acquired during respiration, it may be possible to detect air trapping or bronchial collapse.

In some embodiments, the registration of the plurality of CT scans and the quantitative lung analysis may be used in, for example, pulmonary, surgery and radiology applications. In some embodiments, the described system and method may be used to develop a broad array of image-based techniques, including the characterization of lung biomechanics (to evaluate specific diseases and drug response), generate patient-specific outcomes predictions for invasive techniques such as lobectomy or lung volume reduction surgery, provide early diagnosis techniques for high-risk patients, evaluate structural anomalies such as air trapping before they are clinically detectable, possibly allowing for earlier and more effective treatments.

Figure 2:
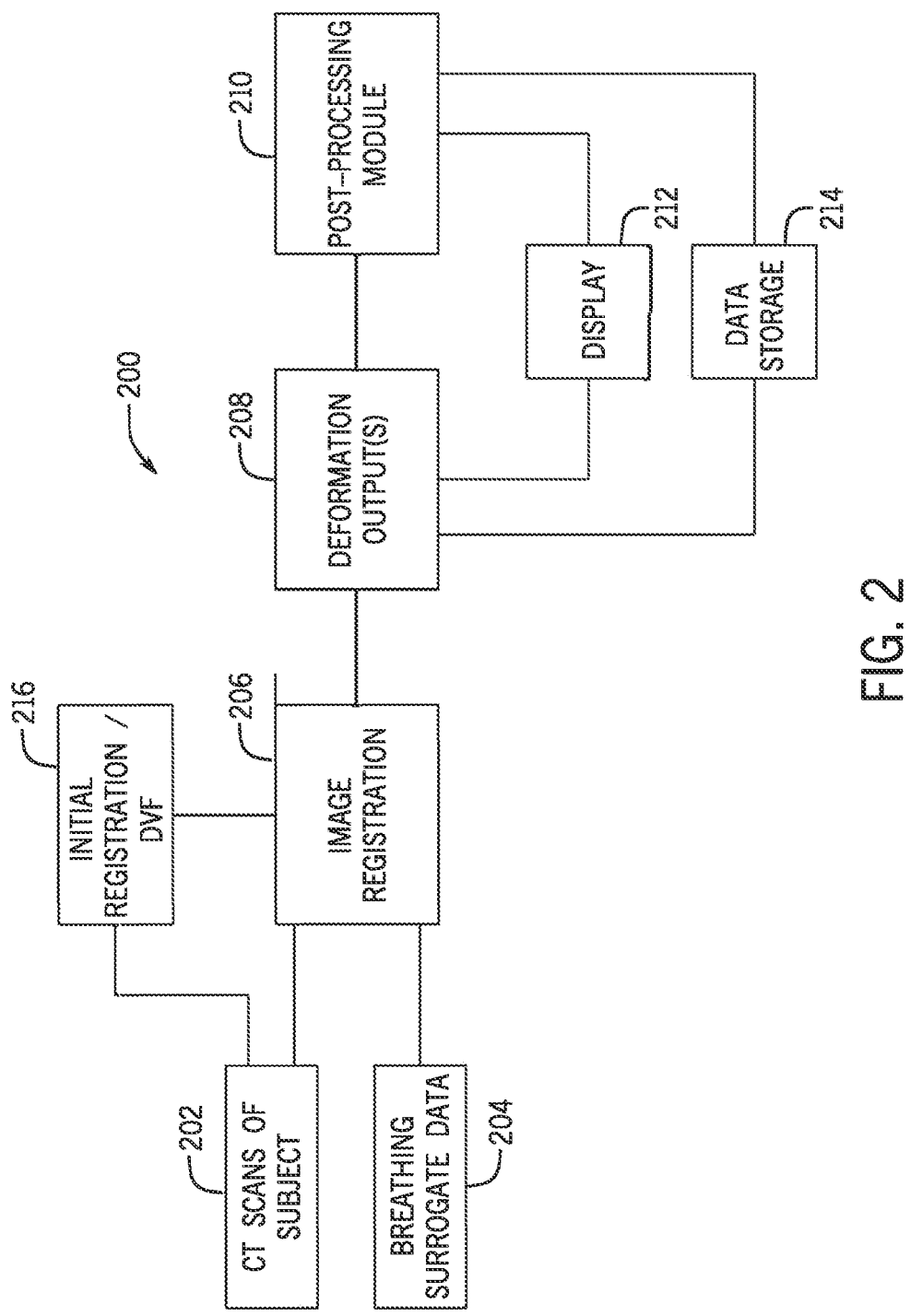
FIG. 2 is a block diagram of a system for simultaneously registering a plurality of CT scans of a region of interest for quantitative lung analysis of a subject in accordance with an embodiment.

FIG. 2 is a block diagram of a system for simultaneously registering a plurality of CT scans of a region of interest of a subject in accordance with an embodiment. The system 200 can include inputs including, for example, a plurality of CT scans 202 of a subject and breathing surrogate data 204, an image registration process (or module) 206, deformation output(s) 208, a post-processing module 210, a display 212, data storage 214, and an initial registration/DVF 216. The plurality of CT scans 202 of a subject may be of a region of interest of the subject that includes the lungs of the subject. The input CT scans 202 may be acquired using a CT system such as, for example, CT system 100 shown in FIGS. 1A-1B. Each CT scan (or CT scan dataset) can include a set of slices acquired during the scan. In some embodiments, the CT scans 202 may be acquired during free-breathing, breath-hold, or other circumstances such that the distortion of the lungs between images is reflective of the patient's breathing (as opposed, for example, to changes in the disease state or pose). As used herein, the term free-breathing is intended as a general description of the subject not holding their breath. Free-breathing may include coached breathing or mechanical ventilation or other methods of modifying or controlling the breathing cycle. In some embodiments, the CT scans 202 may be acquired during modified breathing including breathing during or after exercise or application of a drug. In some embodiments, the input CT scans 202 may be acquired using known free-breathing CT acquisition protocols. For example, a fast helical free-breathing CT (FHFBCT) protocol may be used to acquire the CT scans 202. In some embodiments, the CT scans 202 of the subject are acquired repeatedly in alternating directions. In some embodiments, the plurality of CT scans 202 may be acquired using a relatively low dose (e.g., first scan 160 mAs, subsequent scans 40 mAs). In some embodiments the plurality of input CT scans 202 (or CT scan datasets) are acquired over a single session. In some embodiments, the CT scans 202 may include the entire lungs or subregions (e.g., the upper right lungs) of the lungs. If the full CT scans 202 are larger than the lungs, the CT scan may be cropped (e.g., manually or automatically) to include all of the lungs. A region of interest (ROI) may be selected from the CT scans 202 for registration and quantitative lung analysis. In some embodiments, the ROI may be the entire lungs or subregions of the lungs. In some embodiments, all CT slices in each CT scan may be retained to simplify subsequent time synchronization. In some embodiments, ECG measurements may be added to a free-breathing CT acquisition protocol to allow an analysis of registration fluctuation as a function of the cardiac cycle. In some embodiments, a prospective scanning protocol that employed fewer scans but at optimized breathing phases may be used and may allow the use of fewer scans and consequently lower dose. In some embodiments, the registration and quantitative lung analysis techniques described herein may be used with CT scans acquired using methods to reduce breathing-induced blurring in lung CT scans.

Figure 7:
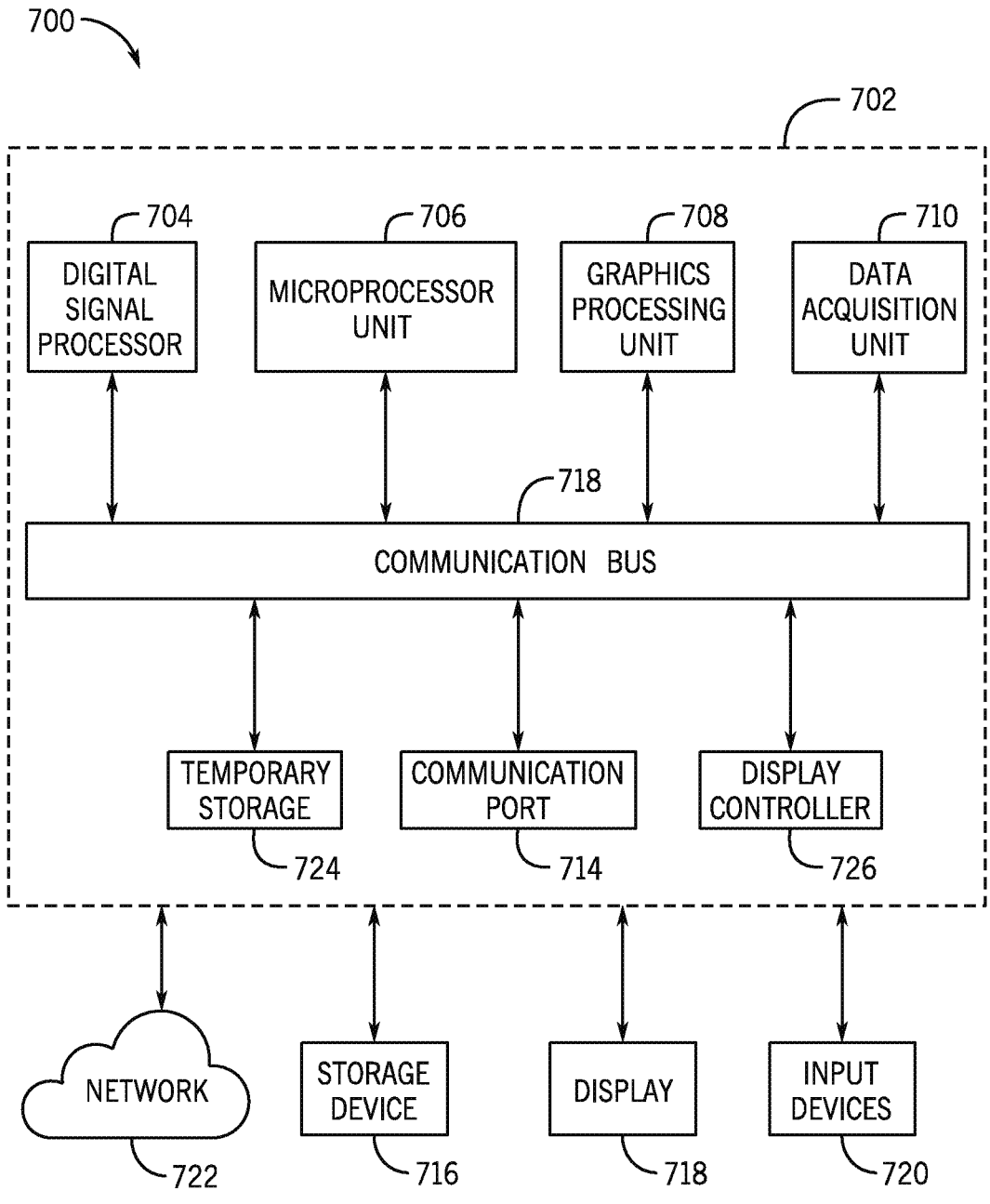
FIG. 7 is a block diagram of an example computer system in accordance with an embodiment.

In some embodiments, the plurality of CT scans 202 of the subject may be retrieved from data storage (or memory) of the system 200, data storage of an imaging system (e.g., data store server 124 of CT system 100 shown in FIG. 1B), or data storage of other computer system (e.g., storage device 716 of computer system 700 shown in FIG. 7). In some embodiments, the plurality of CT scans 202 of the subject may be acquired in real time from a subject using a CT system (e.g., CT system 100 shown in FIGS. 1A-1B). For example, CT scan datasets may be acquired from a subject using a known CT imaging protocol. The acquired CT scans 202 may be provided to the image registration process 206 in real-time from the CT system (e.g., from data store server 124 of the CT system 100 shown in FIGS. 1A-1B), for example, the CT system 100 may acquire CT data and reconstruct the slices in each CT scan in the plurality of CT scans 202 (e.g., using image reconstruction system 126) using known reconstruction methods.

In some embodiments, the inputs to system 200 may also include an initial registration/deformation vector field (DVF) 216. A known image registration method (e.g., a deformation image registration) may be used to process the plurality of CT scans 202 to generate an initial deformation, for example, a DVF. The initial DVF may be utilized by the image registration process 206 as discussed further below. In some embodiments, the initial DVF 216 may be retrieved from data storage (or memory) of the system 200, data storage of an imaging system (e.g., data store server 124 of CT system 100 shown in FIG. 1B), or data storage of other computer system (e.g., storage device 716 of computer system 700 shown in FIG. 7).

In some embodiments, the inputs to system 200 may also include breathing surrogate data 204. For purposes of this description, a surrogate may be used that was measured during CT acquisition of the CT scans 202 and is reflective of the patient's breathing amplitude (A), defined as being a signal functionality related to breathing tidal volume. In some embodiments, the surrogate is measured externally. For example, an abdominal pneumatic bellows may be used as a real-time breathing surrogate to monitor and record the breathing (e.g., a breathing state) of the subject simultaneously with the acquisition of the CT images 202. In some embodiments, the surrogate may be obtained or extracted from the scan data (i.e. from the CT scans or CT scan datasets 202) itself. In some embodiments, the breathing surrogate data 204 includes a breathing amplitude (A). The breathing amplitude, A, may be derived from the surrogate. The surrogate may be synchronized with the CT scan acquisition so that the amplitude can be assigned to each slice in the scan as related to the CT slice acquisition time. The breathing amplitude, A, is intended to act as a biomechanically sound value that is related proportionally to breathing tidal volume. Examples of breathing amplitude values include, but are not limited to, abdomen height, diaphragm position, and pneumotachometer-measured tidal volume. Advantageously, in some embodiments, only the breathing amplitude may be needed as the input breathing surrogate data 204. In some embodiments, simultaneous to the breathing surrogate, a CT-on signal may be recorded from the CT system (e.g., at a rate of 100 Hz). In some embodiments, both the breathing surrogate (e.g., an internal bellows air pressure) and the CT-on signal may be recorded in real time. In some embodiments, a breathing amplitude may be calibrated as discussed further below with respect to FIG. 6.

In some embodiments, the breathing surrogate data 204 for the subject may be retrieved from data storage (or memory) of the system 200, data storage of an imaging system (e.g., data store server 124 of CT system 100 shown in FIG. 1B), or data storage of other computer systems (e.g., storage device 716 of computer system 700 shown in FIG. 7). In some embodiments, the breathing surrogate data 204 for the subject may be acquired in real time from a subject using a breathing surrogate and acquired simultaneously with the real-time acquisition of the CT scans 202 using a CT system (e.g., CT system 100 shown in FIGS. 1A-1B). The breathing surrogate data 204 may be provided to the image registration process 206 in real-time from the breathing surrogate.

The CT scans (or CT scan datasets) 202 of the subject, the breathing surrogate data 204, and the initial DVF 216 may be provided as an input to the image registration process (or module) 206. In some embodiments, the image registration module 206 may be configured to perform a deformable image registration to determine the relative positions of the lung tissues throughout the plurality of input CT scans 202. The image registration process 206 may be configured to determine a deformation, for example, a deformation vector field (DVF). The image registration process 206 may employ an objective function which provides a description of the image characteristics that compare the plurality of CT images 202. The objective function may include multiple terms, with each term intended to assert a physical principle. As discussed further below with respect to FIGS. 3A-5, in some embodiments, the objective function may advantageously employ two terms, namely, a first term based on a ventilation-adjusted (or corrected) Hounsfield Unit (HU) difference and a second term based on the conservation-of-mass that denotes a difference between the deformation Jacobian and a tissue density ratio. The image registration process 206 may generate one or more deformation outputs 208. For example, an iterative optimization process may be used to determine the deformation (e.g., a DVF) that minimizes the objective function. Known iterative optimization processes may be used to determine the deformation. The deformation output(s) 208 may be displayed on a display 212 (e.g., displays 118, 144 of the CT system 100 shown in FIG. 1B or display 718 of the computer system 700 shown in FIG. 7). The deformation output(s) 208 may also be stored in data storage, for example, data storage 214 (e.g., data store server 124 of the CT system 100 shown in FIG. 1B or device storage 716 of computer system 700 shown in FIG. 7).

Post-processing module 210 may be configured to perform further processing on the deformation output(s) 208 (e.g., a DVF) of the image registration process 206. In some embodiments, the post-processing module 208 may be configured to determine or estimate one or more quantitative lung parameters such as, for example, ventilation measurements (e.g., local tissue expansion), lung motion measurements and description, breathing dynamics, biomechanical properties, high spatial resolution dynamic ventilation processes, and other structural and functional properties. As discussed further below with respect to FIGS. 3A-5, in some embodiments, ventilation may be calculated voxel-by-voxel as the slope of a first order fit (e.g., a linear fit) or other parameterization of the deformation Jacobian (or Jacobian DVF) as a function of the breathing amplitude. Accordingly, the plurality of CT scans may be used directly to measure ventilation. The outputs of the post-processing module 210 may be displayed on the display 212. The outputs of the post-processing module 210 may also be stored in a data storage, for example, data storage 214. In some embodiments, the post-processing module 210 may be configured to generate a report indicating the one or more quantitative lung parameters. The report may include, for example, images or maps (e.g., a ventilation map), text or metric based reports, audio reports, and the like. The report may be displayed on the display 212. The outputs of the post-processing module 210 may also be stored in a data storage, for example, data storage 214.

In some embodiments, the image registration process (or module) 206 and the post-processing module 210 may be implemented on one or more processors (or processor devices) of a computer system such as, for example, any general-purpose computing system or device, such as a personal computer, workstation, cellular phone, smartphone, laptop, tablet, or the like. As such, the computer system may include any suitable hardware and components designed or capable of carrying out a variety of processing and control tasks, including steps for receiving CT scan(s) of the subject 202, receiving breathing surrogate data 204, implementing the image registration process (or module) 206, implementing the post-processing module 210, providing the deformation output(s) 208 and/or the post-processing module 210 outputs to a display 212 or storing the deformation output(s) 208 and/or the post-processing module 210 outputs in data storage 214. For example, the computer system may include a programmable processor or combination of programmable processors, such as central processing units (CPUs), graphics processing units (GPUs), and the like. In some implementations, the one or more processor of the computer system may be configured to execute instructions stored in a non-transitory computer readable-media. In this regard, the computer system may be any device or system designed to integrate a variety of software, hardware, capabilities and functionalities. Alternatively, and by way of particular configurations and programming, the computer system may be a special-purpose system or device. For instance, such special-purpose system or device may include one or more dedicated processing units or modules that may be configured (e.g., hardwired, or pre-programmed) to carry out steps, in accordance with aspects of the present disclosure.

Figure 3B:
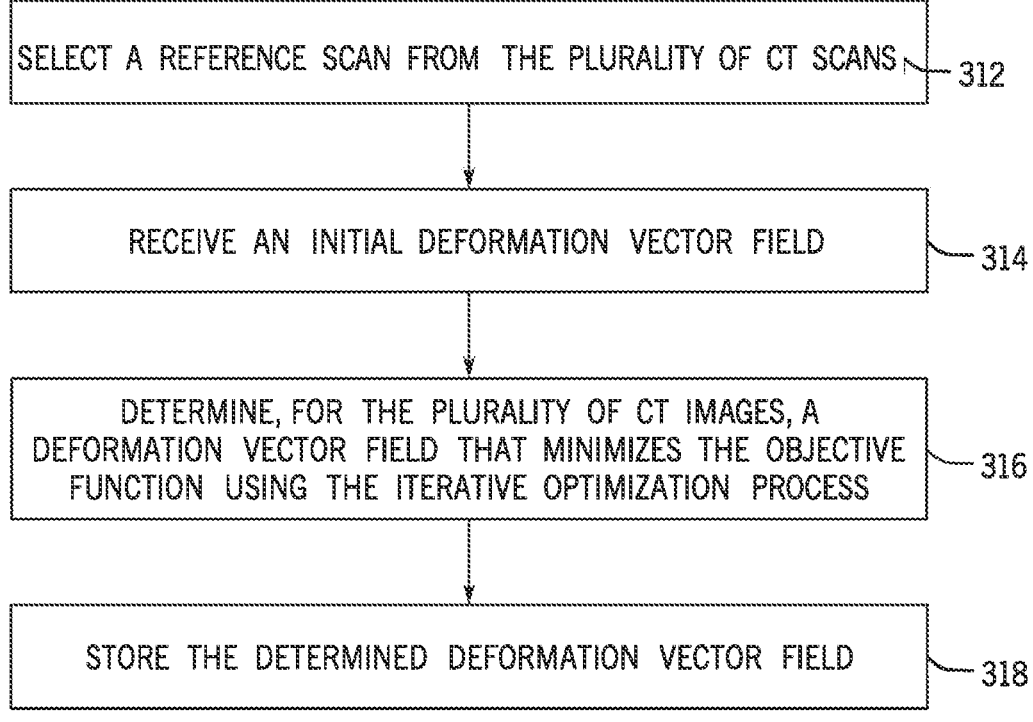

FIGS. 3A and 3B illustrate a method for simultaneously registering a plurality of CT scans of a region of interest of a subject for quantitative lung analysis in accordance with an embodiment. The process illustrated in FIGS. 3A and 3B is described below as being carried out by the system 200 for simultaneously registering a plurality of CT scans of a region of interest of a subject for quantitative lung analysis as illustrated in FIG. 2. Although the blocks of the process are illustrated in a particular order, in some embodiments, one or more blocks may be executed in a different order than illustrated in FIGS. 3A and 3B, or may be bypassed.

In FIG. 3A, at block 302, a plurality of CT scans 202 may be received by an image registration process (or module) 206 from, for example, a CT system (e.g., CT system 100 shown in FIGS. 1A-1B). Each CT scan (or CT scan dataset) in the plurality of CT scans 202 can include a set of slices acquired during the scan. In some embodiments, the plurality of CT scans 202 may be received in real-time from the CT system (e.g., from data store server 124 or image reconstruction system 126 of CT system 100 shown in FIG. 1B), for example, the CT system 100 may acquire CT data for each CT scan and reconstruct the set of CT slices for each CT scan using known reconstruction methods. In some embodiments, the plurality of CT scans 202 may be received from data storage (or memory) of system 200, data storage of an imaging system (e.g., data storage of CT system 100 shown in FIGS. 1A-1B) or data storage of other computer systems (e.g., storage device 716 of computer system 700 shown in FIG. 7). As discussed above, the plurality of CT scans 202 may be acquired during free-breathing, breath-hold, or other circumstances such that the distortion of the lungs between images is reflective of the patient's breathing (as opposed, for example, to changes in the disease state or pose). In some embodiments, the CT scans 202 may be acquired during modified breathing including breathing during or after exercise or application of a drug. In some embodiments, the input CT scans 202 may be acquired using known free-breathing CT acquisition protocols such as, for example, a fast helical free-breathing CT (FHFBCT) protocol. In some embodiments, the CT scans 202 may include the entire lungs or subregions (e.g., the upper right lungs) of the lungs. If the full CT scans 202 are larger than the lungs, the CT scan may be cropped (e.g., manually or automatically) to include all of the lungs. A region of interest (ROI) may be selected from the CT scans 202 for registration and quantitative lung analysis. In some embodiments, the ROI may be the entire lungs or subregions of the lungs. In some embodiments, all CT slices in each CT scan may be retained to simplify subsequent time synchronization.

At block 304, breathing surrogate data 204 may be received by the image registration process (or module) 206 from, for example, a breathing surrogate. As discussed above, in some embodiments, the surrogate is measured externally. For example, an abdominal pneumatic bellows may be used as a real-time breathing surrogate to monitor and record the breathing (e.g., a breathing state) of the subject simultaneously with the acquisition of the CT scans 202. In some embodiments, the surrogate may be obtained or extracted from the image data (i.e. from the CT scans 202) itself. In some embodiments, the breathing surrogate data 204 includes a breathing amplitude (A). The breathing amplitude A may be derived from the surrogate. The surrogate may be synchronized with the CT scan acquisition so that the amplitude can be assigned to each CT slice in the scan as related to the CT slice acquisition time. In some embodiments, the breathing surrogate data 204 may be received in real-time from the breathing surrogate. In some embodiments, the breathing surrogate data 204 may be received from data storage (or memory) of system 200, data storage of the breathing surrogate, or data storage of other computer systems (e.g., storage device 716 of computer system 700 shown in FIG. 7).

At block 306, the image registration process 206 may be used to determine a deformation (e.g., deformation output 208) based on the plurality of CT scans 202 and the breathing surrogate data 204 (e.g., a breathing amplitude) using an iterative optimization process of an objective function. Advantageously, the objective function employed by the image registration process 206 to register the plurality of CT scans 202 may include two terms, namely, a first term based on an approximation of local changes in Hounsfield Units (HU) adjusted for breathing of the subject and a second term based on error in the conservation of mass. The following is an embodiment of the objective function between two of the CT scans, i and j:

$$\left\| HU_i' - HU_j' \right\|_p + \alpha \left\| \Delta\Gamma_{ij} \right\|_p \qquad \text{Eq. 1}$$

where HU are Hounsfield units of the scans within the lung boundary, $\alpha$ is a parameter used to adjust the relative importance of the two terms, $\Delta\Gamma_{ij}$ (see Equation 3 below) is a mathematical description of the conservation of mass, and i and j refer to the scan datasets such that i≠j. In Equation 1, p is the $\ell$p norm. In some embodiments, the two-norm or Euclidian norm, p=2, may be used.

Figure 4:
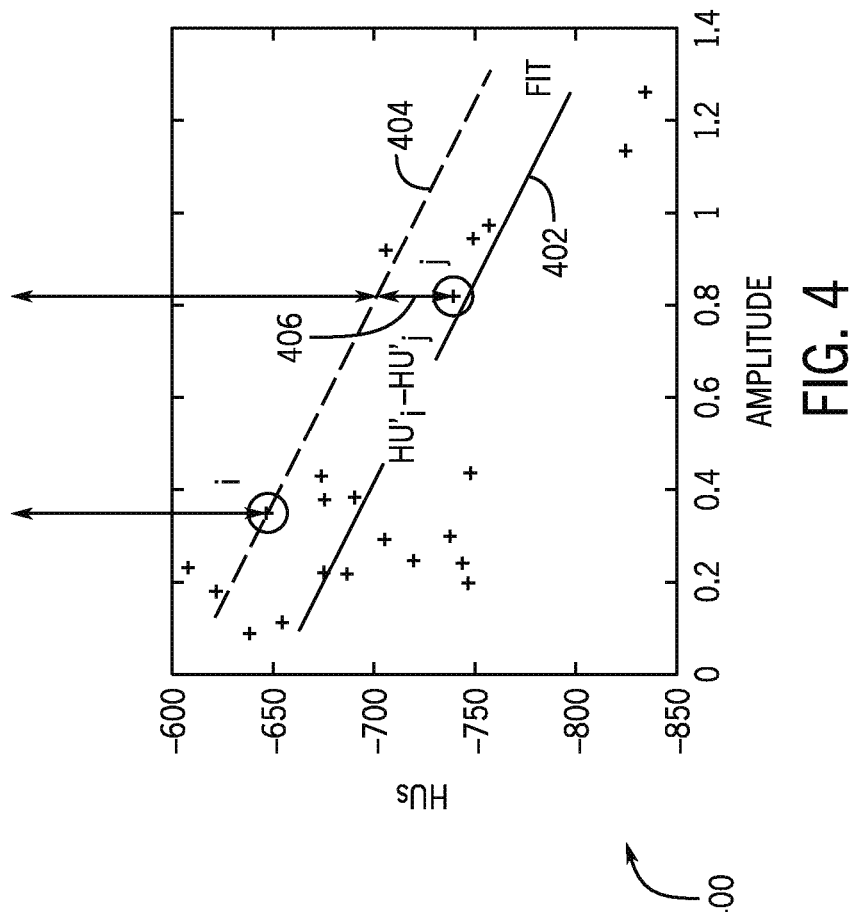
FIG. 4 shows an example graph of ventilation-corrected HU difference in accordance with an embodiment.

One challenge of comparing multiple lung CT scans is that the image intensities (Hounsfield Units) vary because the lungs expand. In order to manage this, a method of approximating the local change in the HU based on breathing and compensating for that change when taking the difference (denoted by the prime symbol) may be used as the first term of the objective function. The equation for HU' may be given by:

$$\left( HU_i' - HU_j' \right) = \left( HU_i - HU_j \right) + \frac{dHU}{dA}(A_j - A_i) \qquad \text{Eq. 2}$$

where $HU_i$ is the HU value of scan i, $HU_j$ is an HU value of scan j, dHU/dA is the slope of a fit of all HUs (scans i, j, and the remaining scan datasets) to their respective amplitudes (e.g. based on a linear fit), $A_i$ is the surrogate amplitude of scan i, and $A_j$ is a surrogate amplitude of scan j. In an embodiment, either i or j may refer to a reference scan. FIG. 4 shows an example graph 400 of ventilation-corrected HU difference in accordance with an embodiment. This example compares points in scans i and j. The solid line 402 is a linear fit to the raw HU values. The dashed line 404 indicates the change in point i to the same amplitude as j. The double arrow 406 indicates the desired ventilation-corrected HU difference. The relationship dHU/dA may be based on a linear fit between the HU values and typically j will be a selected scan termed the reference scan so that all other scan HU' values will be related to the reference scan. In this case, $HU_j' = HU_j$.

Returning to block 306 of FIG. 3A, in some embodiments, the first objective function term may be intended to localize high contrast objects such as blood vessels. If the lung tissue density did not change between scans, the first objective function term would simply be the difference between the reference and target HU values. A mentioned above, in order to compensate for the local ventilation-induced variation in parenchymal HU values, the voxel-specific HU term may be modified by using what may be termed ventilation-corrected HUs. This process can provide an estimate of the variation in HUs with respect to breathing amplitude that can be relatively insensitive to voxel-to-voxel noise.

As mentioned above, the second objective function term may be based on conservation of mass and may be configured to compare the scan Jacobian and the local tissue density ratio. In some embodiment, the second objective function term can serve to guide the registration such that the DVF Jacobians reflected the measured density differences between the scans. It is advantageous to include mass conservation as a term in the objective function used for CT image registration as it may be integral to making sure the DVF is not misbehaved. The term in Equation 1, $\Delta\Gamma_{ij}$, is intended to model conservation of mass errors caused by registration errors. Conservation of mass is a concept that mass cannot be created or destroyed in a closed system. The lungs are not closed, but the majority of mass going in and out of the lungs are air, which has negligible density compared to soft tissues. The other material that enters or leaves is blood, which increases or decreases by about 50 ml during the heartbeat, out of a total lung volume of approximately 5 l. Therefore, the blood volume can either be considered or ignored, depending on the application.

The equation for conservation of mass ignoring blood pool changes may be given by:

$$\Delta\Gamma_{ij} = \frac{J_{ij} - \rho_i/\rho_j}{\sqrt{2}} \qquad \text{Eq. 3}$$

where J is the Jacobian of the DVF (essentially the local expansion), $\rho_i$ is a tissue density determined by scan i, and $\rho_j$ is a tissue density determined by scan j. The Jacobian of the DVF may be defined as the determinate of the Jacobian matrix of the DVF plus the identity matrix. For clarity, the Jacobian matrix is labeled here $J_m$ $$J_m = \begin{vmatrix} \dfrac{\partial X}{\partial x} & \dfrac{\partial X}{\partial y} & \dfrac{\partial X}{\partial z} \\ \dfrac{\partial Y}{\partial x} & \dfrac{\partial Y}{\partial y} & \dfrac{\partial Y}{\partial z} \\ \dfrac{\partial Z}{\partial x} & \dfrac{\partial Z}{\partial y} & \dfrac{\partial Z}{\partial z} \end{vmatrix} \qquad \text{Eq. 4}$$

Where X, Y, and Z correspond to the DVF in the x, y, and z directions, respectively. The Jacobian is the determinate of $J_m$+I where I is the identity matrix.

$$J = \det\,(J_m + I) \qquad \text{Eq. 5}$$

Figure 5:
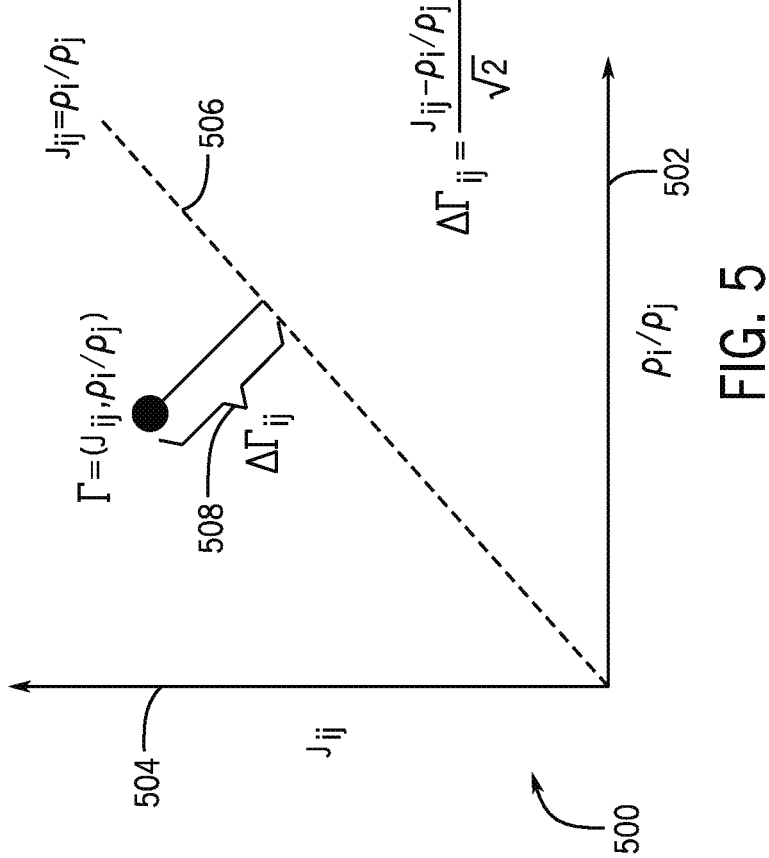
FIG. 5 is a schematic showing a definition of $\Delta\Gamma$ in accordance with an embodiment.

The tissue density ($\rho$) is typically calculated from the HU using a linear relationship determined at the time of CT calibration by sampling regions with air and known tissue or materials (e.g., blood). FIG. 5 is a graph 500 showing the definition of $\Delta\Gamma$ in accordance with an embodiment. Graph 500 illustrates the relationship between the DVF Jacobian and the tissue density ratio of a voxel represented in scans i and j. The axes 502 and 504 are the density ratio and the Jacobian of the region (e.g., voxel) of images i and j, respectively. The conservation of mass dictates that the change in density needs to be offset by the local expansion (mathematically described by the Jacobian). Therefore, for mass conservation, the two should be equal, so all points should lie somewhere on the 45 degree line (dashed) 506 (i.e., the line corresponding to $J_{iR}=\rho_R/\rho_i$). Errors in either the Jacobian (vis a vis the DVF) or the density (e.g., noise or misregistration) can cause this relationship to be broken. To quantify this, the location of the point 508 in this graph 500 is defined as $\Gamma$. The distance (e.g., the Euclidian distance) between the point 508 and the 45 degree line 506 that defines the conservation of mass is $\Delta\Gamma$.

Returning to block 306 of FIG. 3A, one challenge of using Equation 3 is that for much of the lung, the density $\rho$ is small, and with image noise, the denominator of the ratio $\rho_i/\rho_j$ can get very small. Therefore, in some embodiments, equation 3 can be used as the second term or its inverse, which also complies with the conservation of mass, may be used as the second term and may be given by:

$$\Delta\Gamma'_{ij} = \frac{1/J_{ij} - \rho_j/\rho_i}{\sqrt{2}} \qquad \text{Eq. 6}$$

In some embodiments, the terms $\Delta\Gamma$ and $\Delta\Gamma'$ may be used in combination to reduce the impact of image noise on the registration process.

The objective function used for an image registration process may not in itself be mathematically sufficient to assure that the subsequent deformation description (also termed deformation vector field (DVF) is physical. For example, if the objective function is simply the difference between two scan's intensities, the deformation process could connect regions of each scan with the same values, regardless of whether the subsequent DVF was in any way physically possible. Parts could cross or move in arbitrary directions just to minimize the objective function. A useful feature of the $\Delta\Gamma$ objective function term described above is its natural DVF regularization. Without regularization, the $\Delta$HU term would in principle allow unphysical deformations as long as it minimized the HU differences, but the use of the DVF Jacobian in the $\Delta\Gamma$ term can serve to regularize the DVF behavior. In some embodiments, no additional regularization terms are used. In some embodiments, additional regularization terms may be used.

As mentioned, the image registration process 206 may be used to determine a deformation based on the plurality of CT scans 202 and the breathing surrogate data 204 (e.g., a breathing amplitude). FIG. 3B illustrate an example image registration process in accordance with an embodiment. At block 312, a reference scan may be selected from the plurality of CT scans 202 to be registered, for example, the first scan acquired may be used as the reference scan. At block 314, an initial deformation vector field (DVF) may be received. A known image registration method (e.g., a deformation image registration) may be used to process the plurality of CT scans 202 to generate an initial deformation, for example, a DVF. Accordingly, in some embodiments, the image registration process 206 may be used to fine tune the initial registration (i.e., the initial DVF). In some embodiments, the initial DVF 216 may be retrieved from data storage (or memory) of the system 200, data storage of an imaging system (e.g., data store server 124 of CT system 100 shown in FIG. 1B), or data storage of other computer system (e.g., storage device 716 of computer system 700 shown in FIG. 7. Known methods may be used to describe the DVF including, for example, thin-plate splines, optical flow, B-splines, and Demons. At block 316, a DVF (e.g., deformation output 208) for the plurality of CT images 202 that minimizes the objective function described above (Equation 3) may be determined using an iterative optimization process. Known iterative optimization processes may be used to determine the DVF. At block 318, the DVF determined at block 316 may be stored in data storage, for example, data storage 214.

Return to FIG. 3A, once the deformation (e.g., a DVF) has been determined at block 306, the deformation may be used to determine or estimate at least one quantitative lung parameter at block 308 (e.g., using post-processing module 210). The quantitative lung parameters can include, for example, ventilation measurements (e.g., local tissue expansion), lung motion measurements and description, breathing dynamics, biomechanical properties, high spatial resolution dynamic ventilation processes, and other structural and functional properties.

In some embodiments, one of the applications of the CT scan registration is to measure local ventilation. Ventilation is defined herein as the local lung expansion during breathing. The local expansion may be quantified by the Jacobian (defined in Equation 5) and the relationship between the Jacobian and the breathing amplitude A may be used to define the local ventilation. In some embodiment, the ventilation may be defined as a parameterization of the deformation Jacobian (or Jacobian DVF) as a function of the breathing amplitude. For example, in some embodiments, the ventilation V may be defined as the rate of change of the Jacobian with respect to the Amplitude as given by:

$$V = \frac{dJ}{dA} \qquad \text{Eq. 7}$$

Accordingly, the ventilation may be determined by fitting the Jacobian to amplitude. In some embodiments, the analysis to determine ventilation may be conducted on a voxel-by-voxel basis. Equation 7 can be subdivided into amplitudes or patient breathing patterns (e.g., coached versus uncoached) or that are acquired during inspiration and expiration to evaluate changes in ventilation during specific breathing conditions.

At block 310, the deformation and the at least one quantitative lung parameter may be displayed on the display 212. The deformation and the at least one quantitative lung parameter may also be stored in a data storage, for example, data storage 214. In some embodiments, the post-processing module 210 may be configured to generate a report indicating the one or more quantitative lung parameters. The report may include, for example, images or maps (e.g., a ventilation map), text or metric based reports, audio reports, and the like. The report may be displayed on the display 212. The outputs of the post-processing module 210 may also be stored in a data storage, for example, data storage 214

As mentioned above, the breathing surrogate data 204 used by the image registration process 206 may be a breathing amplitude derived from a breathing surrogate. In some embodiments, an abdominal pneumatic bellows may be used as a real-time breathing surrogate to monitor and record the breathing (e.g., a breathing state) of the subject simultaneously with the acquisition of the CT images 202 However, the bellows may have a known signal drift that may need to be measured and removed in order to provide a useful surrogate. Accordingly, in some embodiments, the breathing amplitude may be calibrated (or corrected). In some embodiments, the diaphragm dome may be used to both remove the drift and fine-tune the CT synchronization time offset. Due to motion-induced blurring of the diaphragm, one of the CT scans with minimal blurring may be selected as the reference for this calibration process (i.e., the drift-correction reference scan). A point near the diaphragm dome may be manually selected on the drift-correction reference scan. In some embodiments, this point can be used as the center of a voxel column array and the diaphragm within each column can be crudely aligned using rigid registration. CT scan profiles through a subsequent array of voxel columns, oriented craniocaudally and centered on the selected voxel may be extracted and blurred using, for example, a standard deviation one-dimensional Gaussian kernel. The blurring can allow the CT Hounsfield profiles in scans with and without motion blurring to be subsequently fit to error functions. The error function fit residuals may be calculated and profiles with the largest residuals may be observed to intersect vessels or other structures within the parenchymal tissues. In some embodiments, in order to remove these profiles from subsequent analysis, only profiles with root-mean square residual HUs of less than a predetermined value may be retained. The mean differences between the drift-correction reference scan and other scans' error function inflection points may be used as the relative diaphragm shift measurement.

Figure 6:
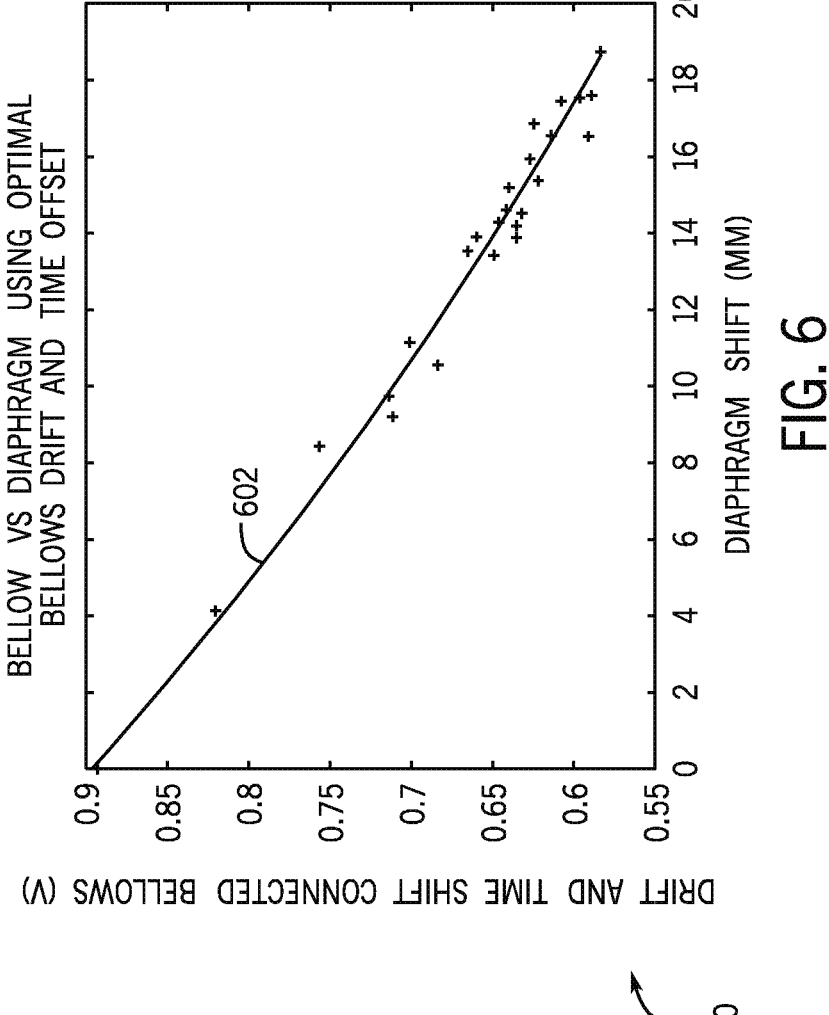
FIG. 6 shows an example of the relationship between a drift and time corrected bellows signal and corresponding relative diaphragm shifts used as a breathing amplitude for a patient in accordance with an embodiment.

FIG. 6 shows an example graph 600 of the relationship between the drift and time corrected bellows signal and the corresponding relative diaphragm shifts used as the breathing amplitude in accordance with an embodiment. The line 602 shows the quadratic curve used to convert subsequent corrected bellows signals to diaphragm positions for use as the patient's breathing amplitude. In some embodiments, a minimum fit residual may be used to determine the optimal drift and time offset values. The amplitude measurement error, defined as the root-mean squared residual divided by the $90^{th}$ percentile bellows amplitude range, was 3.3% in this example.

FIG. 7 is a block diagram of an example computer system in accordance with an embodiment. Computer system 700 may be used to implement the systems and methods described herein. In some embodiments, the computer system 700 may be a workstation, a notebook computer, a tablet device, a mobile device, a multimedia device, a network server, a mainframe, one or more controllers, one or more microcontrollers, or any other general-purpose or application-specific computing device. The computer system 700 may operate autonomously or semi-autonomously, or may read executable software instructions from the memory or storage device 716 or a computer-readable medium (e.g., a hard drive, a CD-ROM, flash memory), or may receive instructions via the input device 720 from a user, or any other source logically connected to a computer or device, such as another networked computer or server. Thus, in some embodiments, the computer system 700 can also include any suitable device for reading computer-readable storage media.

Data, such as data acquired with an imaging system (e.g., a CT imaging system) may be provided to the computer system 700 from a data storage device 716, and these data are received in a processing unit 702. In some embodiment, the processing unit 702 includes one or more processors. For example, the processing unit 702 may include one or more of a digital signal processor (DSP) 704, a microprocessor unit (MPU) 706, and a graphics processing unit (GPU) 708. The processing unit 702 also includes a data acquisition unit 710 that is configured to electronically receive data to be processed. The DSP 704, MPU 706, GPU 708, and data acquisition unit 710 are all coupled to a communication bus 712. The communication bus 712 may be, for example, a group of wires, or a hardware used for switching data between the peripherals or between any component in the processing unit 702.

The processing unit 702 may also include a communication port 714 in electronic communication with other devices, which may include a storage device 716, a display 718, and one or more input devices 720. Examples of an input device 720 include, but are not limited to, a keyboard, a mouse, and a touch screen through which a user can provide an input. The storage device 716 may be configured to store data, which may include data such as, for example, acquired data, acquired scans, deformation data, ventilation measurements, etc., whether these data are provided to, or processed by, the processing unit 702. The display 718 may be used to display images and other information, such as CT images, patient health data, and so on.

The processing unit 702 can also be in electronic communication with a network 722 to transmit and receive data and other information. The communication port 714 can also be coupled to the processing unit 702 through a switched central resource, for example the communication bus 712. The processing unit can also include temporary storage 724 and a display controller 726. The temporary storage 724 is configured to store temporary information. For example, the temporary storage 724 can be a random access memory.

Computer-executable instructions for simultaneously registering a plurality of computed tomography (CT) scans of a region of interest of a subject for quantitative lung analysis according to the above-described methods may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital volatile disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for simultaneously registering a plurality of computed tomography (CT) scans of a region of interest of a subject including a subject's lungs for quantitative lung analysis, the method comprising:

receiving a plurality of CT scans of the region of interest acquired with a CT imaging system;

receiving a breathing surrogate data for the subject, the breathing surrogate data comprising an amplitude for each of the plurality of CT scans; and determining a deformation based on the plurality of CT scans and the breathing surrogate data using an iterative optimization process of an objective function having a first term based on an approximation of local changes in Hounsfield Units (HU) adjusted for breathing of the subject and a second term based on error in the conservation of mass.

2. The method according to claim 1, wherein the deformation is a deformation vector field (DVF).

3. The method according to claim 1, wherein the objective function is given by:

$$\left\| HU_i' - HU_j' \right\|_p + \alpha \| \Delta\Gamma_{ij} \|_p$$

where HU are Hounsfield units of the CT scans within a lung boundary, $\alpha$ is a parameter used to adjust the relative importance of the first term and the second term, $\Delta\Gamma_{ij}$ is a mathematical description of the conservation of mass, i and j refer to scans such that i≠j, and p is the $\ell$ p norm.

4. The method according to claim 3, wherein the first term is given by:

$$\left( HU_i' - HU_j' \right) = (HU_i - HU_j) + \frac{dHU}{dA}(A_j - A_i)$$

where HU, is an HU value of scan i, $HU_j$ is an HU value of scan j, dHU/dA is a slope of a fit of all HUs to their respective amplitudes, $A_i$ is a surrogate amplitude of scan i, $A_j$ is a surrogate amplitude of scan j, and one of i and j is a reference scan.

5. The method according to claim 3, wherein the second term is given by one of:

$$\Delta\Gamma_{ij} = \frac{J_{ij} - \rho_i/\rho_j}{\sqrt{2}}$$

or the inverse relationship $$\Delta\Gamma_{ij}' = \frac{1/J_{ij} - \rho_j/\rho_i}{\sqrt{2}}$$

where J is the Jacobian of a deformation vector field (DVF), $\rho_i$ is a tissue density determined by scan i, and $\rho_j$ is a tissue density determined by scan j.

6. The method according to claim 1, further comprising determining at least one quantitative lung parameter based on the deformation.

7. The method according to claim 6, wherein the at least one quantitative lung parameter is ventilation.

8. The method according to claim 7, wherein the ventilation is determined as a parameterization of a Jacobian of a deformation vector field (DVF) as a function of the breathing amplitude.

9. The method according to claim 7, wherein the ventilation (V) is determined as a rate of change of the Jacobian (J) of the deformation vector field (DVF) with respect to breathing amplitude (A) as given by:

$$V = \frac{dJ}{dA}.$$

10. The method according to claim 1, wherein each CT scan in the plurality of CT scans is acquired during free-breathing.

11. The method according to claim 1, wherein each CT scan in the plurality of CT scans is acquired during modified breathing.

12. The method according to claim 1, wherein the amplitude is calibrated based on a position of a diaphragm dome of the subject in at least one of the plurality of CT scans.

13. The method according to claim 1, wherein determining a deformation based on the plurality of CT scans and the breathing surrogate data using an iterative optimization process of the objective function comprises determining a deformation vector field that minimizes the objective function.

14. A system for simultaneously registering a plurality of computed tomography (CT) scans of a region of interest of a subject including a subject's lungs for quantitative lung analysis, the system comprising:

a processor device; and a non-transitory computer-readable memory storing instructions executable by the processor device, wherein the instructions, when executed by the processor device, cause the system to:

receive a plurality of CT scans of the region of interest acquired with a CT imaging system;

receive a breathing surrogate data for the subject, the breathing surrogate data comprising an amplitude for each of the plurality of CT scans; and determine a deformation based on the plurality of CT scans and the breathing surrogate data using an iterative optimization process of an objective function having a first term based on an approximation of local changes in Hounsfield Units (HU) adjusted for breathing of the subject and a second term based on error in the conservation of mass.

15. The system according to claim 14, wherein the deformation is a deformation vector field (DVF).

16. The system according to claim 14, wherein the objective function is given by:

$$\left\| HU_i' - HU_j' \right\|_p + \alpha \left\| \Delta\Gamma_{ij} \right\|_p$$

where HU are Hounsfield units of the CT scans within a lung boundary, $\alpha$ is a parameter used to adjust the relative importance of the first term and the second term, $\Delta\Gamma_{ij}$ is a mathematical description of the conservation of mass, i and j refer to scans such that i≠j, and p is the $\ell$ p norm.

17. The system according to claim 16, wherein the first term is given by:

$$\left( HU_i' - HU_j' \right) = (HU_i - HU_j) + \frac{dHU}{dA}(A_j - A_i)$$

where $HU_i$ is an HU value of scan i, $HU_j$ is an HU value of scan j, dHU/dA is a slope of a fit of all HUs to their respective amplitudes, $A_i$ is a surrogate amplitude of scan i, $A_j$ is a surrogate amplitude of scan j, and one of i and j is a reference scan.

18. The system according to claim 16, wherein the second term is given by one of:

$$\Delta\Gamma_{ij} = \frac{J_{ij} - \rho_i/\rho_j}{\sqrt{2}}$$

or the inverse relationship $$\Delta\Gamma_{ij}' = \frac{1/J_{ij} - \rho_j/\rho_i}{\sqrt{2}}$$

where J is the Jacobian of a deformation vector field (DVF), $\rho_i$ is a tissue density determined by scan i, and $\rho_j$ is a tissue density determined by scan j.

19. The system according to claim 14, wherein the instructions, when executed by the processor device, further cause the system to determine at least one quantitative lung parameter based on the deformation.

20. The system according to claim 19, wherein the at least one quantitative lung parameter is ventilation.

21. The system according to claim 20, wherein the ventilation is determined as a parameterization of a Jacobian of a deformation vector field (DVF) as a function of the breathing amplitude.

22. The system according to claim 20, wherein the ventilation is determined as a rate of change of a Jacobian (J) of a deformation vector field (DVF) with respect to breathing amplitude (A) as given by:

$$V = \frac{dJ}{dA}.$$

23. The system according to claim 14, wherein each CT scan in the plurality of CT scans is acquired during free-breathing.

* * * * *